(12) United States Patent
Erickson et al.

(10) Patent No.: US 10,604,733 B2
(45) Date of Patent: *Mar. 31, 2020

(54) OPTOFLUIDIC PHOTOBIOREACTOR APPARATUS, METHOD, AND APPLICATIONS

(71) Applicant: CORNELL UNIVERSITY, Ithaca, NY (US)

(72) Inventors: David Erickson, Ithaca, NY (US); Perry M. Schein, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/351,715

(22) Filed: Nov. 15, 2016

(65) Prior Publication Data

US 2017/0058249 A1  Mar. 2, 2017

Related U.S. Application Data

(63) Continuation-in-part of application No. 13/885,478, filed as application No. PCT/US2011/060557 on Nov. 14, 2011, now Pat. No. 9,518,248.

(Continued)

(51) Int. Cl.
*C12M 1/00* (2006.01)
*G02B 6/293* (2006.01)
(Continued)

(52) U.S. Cl.
CPC ............ *C12M 31/10* (2013.01); *C12M 21/02* (2013.01); *C12N 1/12* (2013.01); *C12N 1/20* (2013.01);
(Continued)

(58) Field of Classification Search
CPC ...... C12M 21/02; C12M 23/22; C12M 23/06; C12M 31/10; C12M 31/02; C12M 31/08;
(Continued)

(56) References Cited

U.S. PATENT DOCUMENTS 5,198,073 A  3/1993 Ishibashi
5,447,629 A  9/1995 Chaumont et al.
(Continued)

FOREIGN PATENT DOCUMENTS

CN  101356261  1/2009
GB  2462332 A  2/2010
(Continued)

OTHER PUBLICATIONS

Eltayeb et al.; Design and modeling of optical modules for use in the "Emerald Forest" algae photobioreactors; Computers & Chemical Engineering, vol. 34, No. 9; pp. 1323-1304; Elsevier Science Ltd.; Sep. 7, 2010; 2011, The Institution of Engineering and Technology.
(Continued)

*Primary Examiner* — Michael L Hobbs
(74) *Attorney, Agent, or Firm* — Bond, Schoeneck & King, PLLC; Blaine Bettinger; William Greener

(57) ABSTRACT

An optofluidic photoreactor including an optical waveguide having an input, characterized by an evanescent optical field confined along an outer surface of the optical waveguide produced by radiation propagating in the optical waveguide, means for inputting light to the input of the optical waveguide, and a photoactive material disposed substantially only within the evanescent field. A method for optically activating a photoactive material in an optofluidic photoreactor to convert carbon dioxide and water into other molecules that may be useful as a fuel or a chemical feedstock.

18 Claims, 11 Drawing Sheets

Related U.S. Application Data

(60) Provisional application No. 61/413,685, filed on Nov. 15, 2010.

(51) Int. Cl.

| | | |
|---|---|---|
| *G02B 6/26* | (2006.01) | |
| *C12P 7/06* | (2006.01) | |
| *G02B 6/00* | (2006.01) | |
| *C12N 1/20* | (2006.01) | |
| *C12N 1/12* | (2006.01) | |
| *C12P 7/04* | (2006.01) | |

(52) U.S. Cl.
CPC ............... *C12P 7/04* (2013.01); *C12P 7/065* (2013.01); *G02B 6/00* (2013.01); *G02B 6/262* (2013.01); *G02B 6/29331* (2013.01); *Y02E 50/17* (2013.01)

(58) Field of Classification Search
CPC ...... C12M 31/12; C12M 31/00; C12M 43/06; C12M 43/08; C12N 13/00; C12P 5/023; C12P 7/649; C02F 3/32; A01G 33/00; Y02E 50/13; Y02E 50/343
USPC ........................................................ 435/292.1
See application file for complete search history.

(56) References Cited

U.S. PATENT DOCUMENTS

| | | | |
|---|---|---|---|
| 5,585,266 | A | 12/1996 | Plitt et al. |
| 5,614,378 | A | 3/1997 | Yang et al. |
| 6,104,452 | A | 8/2000 | Schmutz |
| 6,254,775 | B1 | 7/2001 | McElvaney |
| 9,518,248 | B2 * | 12/2016 | Erickson ............... C12M 21/02 |
| 2005/0176131 | A1 | 8/2005 | Flickinger et al. |
| 2006/0199260 | A1 | 9/2006 | Zhang et al. |
| 2007/0264708 | A1 | 11/2007 | Bayless et al. |
| 2008/0153080 | A1 | 6/2008 | Woods et al. |
| 2009/0047722 | A1 | 2/2009 | Wilkerson et al. |
| 2009/0148931 | A1 * | 6/2009 | Wilkerson ............ C12M 21/02 435/286.1 |
| 2009/0181434 | A1 | 7/2009 | Aikens et al. |
| 2009/0203116 | A1 | 8/2009 | Bazaire |
| 2010/0190227 | A1 | 7/2010 | Jochen et al. |
| 2010/0210001 | A1 * | 8/2010 | Seyfried ............... C12M 21/02 435/257.1 |
| 2011/0076747 | A1 | 3/2011 | Cloud et al. |

FOREIGN PATENT DOCUMENTS

| | | |
|---|---|---|
| JP | 4190782 A | 7/1992 |
| JP | 6225778 A | 8/1994 |
| JP | 7023771 A | 1/1995 |
| KR | 20090038313 A | 4/2009 |
| WO | 1992000380 A1 | 1/1992 |
| WO | 2007129327 A1 | 11/2007 |
| WO | 2009018498 | 2/2009 |
| WO | 2009043763 A1 | 4/2009 |
| WO | 2009116852 A1 | 9/2009 |
| WO | 2010085853 A1 | 8/2010 |
| WO | 2010138657 A1 | 12/2010 |
| WO | 2011069372 A1 | 6/2011 |

OTHER PUBLICATIONS

Energy Economist; Fuel and Food from Algae; NewsRoom 2009(Dialog® File 993): (c) 2011 Dialog.

Frense, D., et al., Detection of environmental pollutants using optical biosensor with immobilized algae cells. Senors and Actuators B: Chemical 51, 256-260, 1998.

Matsunaga, T., et al., Glutamate production from CO2 by Marine Cyanbacterium *Synechococcus* sp. Applied Biochemistry and Biotechnology 28-29, 157-167, 1991.

Mednelson, Y., Optical Sensors. In Encyclopedia of Medical Devices and Instrumentation, Second Edition, vol. 5, Excerpt of p. 161, 2006.

Atsumi, S., et al., Direct photosynthetic recycling of carbon dioxide to isobutyraldehyde. Nature Biotechnology 27, 1177-80, 2009.

Lebeau, T., et al., Algal Cultures, Analogues of Blooms and Applications, Science Publishers, Inc., vol. 2, ed. D. V. Subba Rao, pp. 801-837, 2006.

Hall, D. O. and Rao, K. K., Immobilized Photosynthetic Membranes and Cells for the Production of Fuels and Chemicals, Biotechnological Applications of Lipid Microstructures, 225-245, Springer US 1988.

Mallick, N., Biotechnological potential of immobilization algae for wasterwater N, P and metal removal: A Review, BioMetals 15, 377-390, 2002.

International Search Report and Written Opinion for International Application No. PCT/US2011/060557, dated May 21, 2012, 8 pages.

Office Action issued in related Chinese Application No. 201180065337.5 dated Apr. 4, 2014, 3 pages.

Sugiura, Miwa, et al., Highly Purified Thermo-Stable Oxygen-Evolving Photosystem II Core Complex from the Thermophilic Cyanobacterium *Synechococcus* elongatus Having His-Tagged CP43, Plant Cell Physiol. 40 (12): (1999) pp. 1219-1231.

Ooms, Matthew D., et al., An Optofluidic Photobioreactor Strategy for Bioenergy, ASME 2011 International Mechanical Engineering Congress & Exposition; 3 pages.

Jung, Erica Eunjung, et al., Slab waveguide photobioreactors for microalgae based biofuel production, Lab on a Chip, vol. 12, The Royal Society of Chemistry 2012, pp. 3740-3745.

Erickson, David, et al., Optofluidics for energy applications, Nature Photonics, vol. 5, Oct. 2011, pp. 583-590.

European Search Report issued in related EP Application No. 11841822.7 dated Aug. 21, 2017.

* cited by examiner

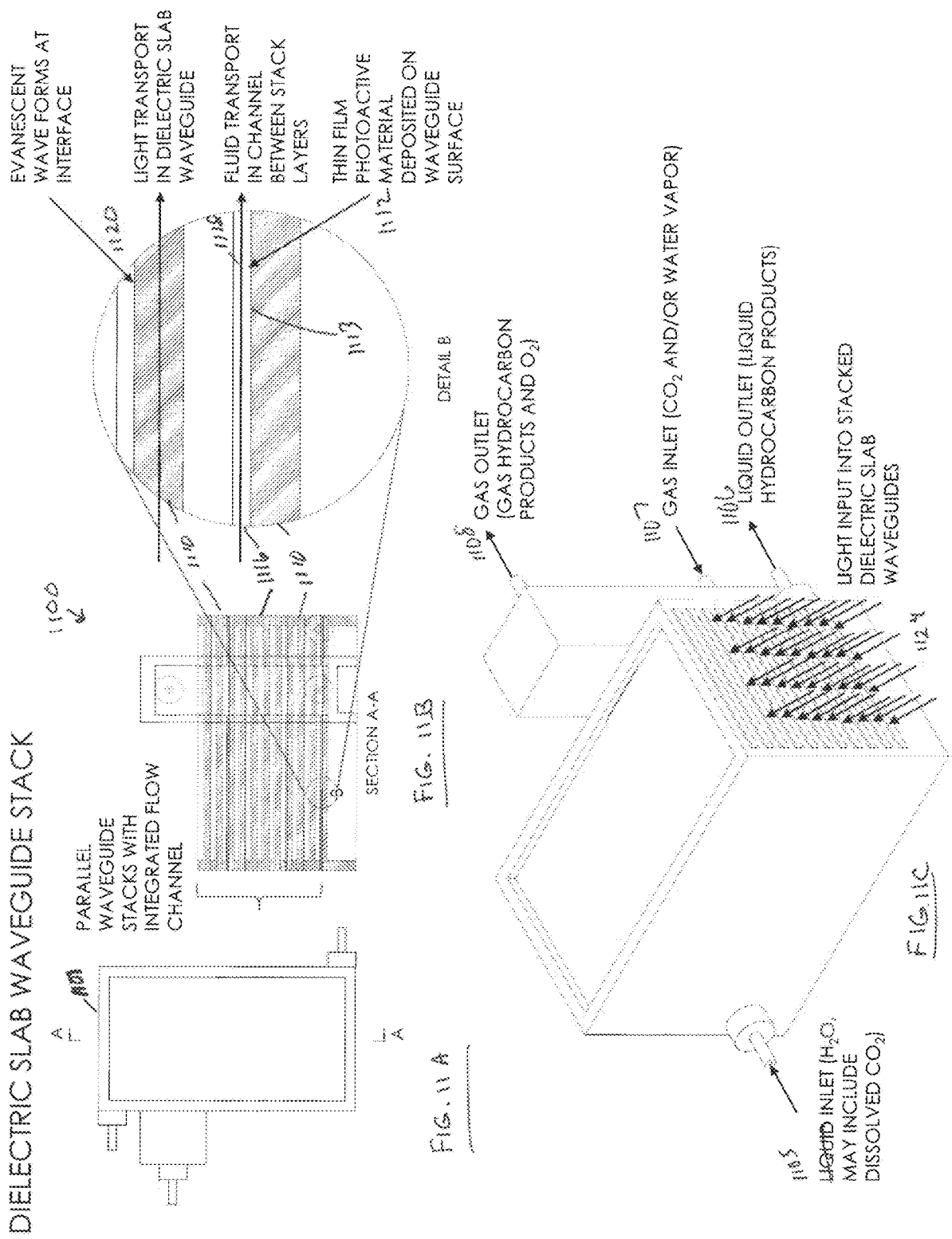

OPTOFLUIDIC PHOTOBIOREACTOR APPARATUS, METHOD, AND APPLICATIONS

CROSS-REFERENCE TO RELATED APPLICATIONS

This application is a Continuation-In-Part of U.S. application Ser. No. 13/885,478 filed on Jul. 30, 2013, now U.S. Pat. No. 9,518,248, which is a US National Phase filing of International Application No. PCT/US2011/060557 filed Nov. 14, 2011 which itself derives priority from U.S. Provisional Patent Application Ser. No. 61/413,685 filed on Nov. 15, 2010, the contents of which are relied upon and incorporated herein by reference in their entireties.

GOVERNMENT SPONSORSHIP

N/A.

BACKGROUND

Field of the Invention

Embodiments of the invention relate generally to photoreactors and associated photoreaction methods and applications. More particularly, embodiments of the invention are directed to optofluidic photoreactor apparatuses and associated methods and applications, in which light is delivered to photoactive materials to perform chemical reactions that convert carbon dioxide and water into other molecules that may be useful as fuels or chemical feedstocks, e.g., a photosynthetically-active entity (e.g., bacteria, algae, or other photosynthetic microorganism) or any photoactive element, including photocatalysts, that can perform the conversion of carbon dioxide and water using optical energy, through the evanescent radiation field from the surface of a waveguide upon which the photoactive material is disposed. Non-limiting embodied applications of the invention pertain to the delivery of said evanescent radiation to said photoactive material to directly or indirectly produce fuels, chemicals, and/or biomass such as, but not limited to, algae, carbon monoxide and hydrogen, and liquid and gas hydrocarbon molecules that can function as, or be further processed to produce chemicals such as, but not limited to, fuel.

Technical Background

The conversion of solar energy to fuel through the cultivation of photosynthetic algae and cyanobacteria relies critically on light delivery to microorganisms. Conventional direct irradiation of a bulk suspension leads to nonuniform light distribution within a strongly absorbing culture, and related inefficiencies.

Growing concern over global climate change and the rising cost of fossil fuels has led to substantial investment and research into alternative fuel sources. For this reason, bioenergy approaches have been developed to produce fuels such as ethanol, methanol, hydrogen and diesel. In order to compete with fossil fuels, however, producing biofuels require large feedstock volumes of inexpensive biomass. Although many feedstocks have been explored, including used cooking oil, food crops, and biowastes, most suffer from low net energy benefit, poor energy density, large footprint requirements and/or insufficient availability. Alternatively, microalgae, which exhibit high growth rates and oil content compared to higher plants and have and have the ability to grow in a range of diverse environments, have been used to produce biofuels. In particular, cyanobacteria use solar energy to convert carbon dioxide and water into biofuel, making possible a near carbon neutral petrochemical alternative.

Cost-effective biofuel production from cyanobacteria is directly linked to the density of cultures within a photobioreactor and its overall volume. Currently, the simplest strategy for cultivation of large volumes of microalgae is an open racetrack-style pond exposed to ambient air and sunlight. However, due to issues related to insufficient light distribution, temperature control, nutrient delivery, contamination, and water consumption, pond operations run at low cell densities. As a result, pond strategies suffer from poor areal productivity and low overall power density. Consequently, fully enclosed photobioreactors have been designed to provide precise control over the cultivation environment and maintain growth conditions. However, a central problem common to both open and closed cultivation strategies remains the efficient delivery of light to the microorganisms. As cultures increase in both volume and density, it becomes increasingly difficult for light to be distributed evenly to the individual bacteria. In current reactors, areas near the exposed surface tend to be overexposed, resulting in photoinhibition, and large interior regions are effectively in darkness. Flowing, dilute solutions must be employed to circulate bacteria through regions with productive light levels, placing a fundamental limit on culture density and overall power density of this technology.

A variety of photobioreactor strategies have been developed to provide more effective light distribution to cells by spatially diluting the light over a larger surface area. One strategy is to use light guides to channel light into the reactor volume and subsequently scatter the light into the media. Our reported approach employed cylindrical glass light distributors inserted into a culture tank to assist in distributing light. Sunlight harvested from arrays of Fresnel lenses was channeled to the reactor via optical fiber. Another reported approach used side-lit optical fibers inserted into the culture tank to improve light delivery. Another used optical fibers inserted into the culture chambers with the goal of scattering light collected from external solar collectors into the culture. Although these early studies indicate that increasing control and irradiated surface area within a photobioreactor can improve productivity, these technologies do not escape the fundamental limitation posed by the overexposure and shadowing issues accompanying direct irradiation of bulk cultures.

An evanescent field is a nearfield standing wave having an intensity that exhibits exponential decay with distance from the boundary at which the wave was formed. Evanescent waves are formed when waves traveling in a medium (e.g., an optical waveguide) via total internal reflection strike the boundary at an angle greater than the critical angle. Evanescent field phenomena are well known in the art.

In view of the problems and shortcomings identified above and known in the art, the embodied invention provides solutions and advantageous approaches that will benefit and advance the state of the art in this and related technologies.

SUMMARY OF THE INVENTION

An embodiment of the invention is directed to an optofluidic photobioreactor. The bioreactor includes an optical waveguide having an input, characterized by an evanescent optical field confined along an outer surface of the optical waveguide that is produced by radiation propagating in the optical waveguide, and a selected photosynthetic microorganism disposed substantially within the evanescent field. As will be more fully understood from the detailed description below, the evanescent field advantageously extends from the waveguide for a distance on the order of the thickness (i.e., minor diameter) of the photosynthetic microorganism that is being irradiated by the evanescent field, thus the microorganism will be understood to be disposed substantially within the evanescent field. According to various non-limiting, exemplary aspects:

the optical waveguide is an unclad optical fiber having a diameter, d, where 10 μm≤d≤100 μm, and an input end;

the optical waveguide is a multi-mode optical fiber;

the photobioreactor further includes two or more optical waveguides disposed in a side-by-side array configuration and having a center-to-center intra-waveguide separation, D, where d≤D≤1.5 d;

the photobioreactor further includes a photobioreactor enclosure having an input and an output, inside of which the two or more optical waveguides are disposed, wherein the photobioreactor enclosure is characterized by a plurality of optically-dark fluid channels created by a void space surrounding the plurality of optical waveguides;

the optical waveguide further comprises a prism waveguide;

the photobioreactor further includes means for inputting light to the input of the optical waveguide;

the means for inputting light to the input of the optical waveguide comprises a laser output directly input to a prism waveguide;

the means for inputting light to the input of the optical waveguide comprises solar radiation channeled to the input of the optical waveguide;

the photobioreactor includes a liquid microorganism-nutrient media disposed in a void space of the photobioreactor;

the photobioreactor includes a controller operably connected to the photobioreactor enclosure;

the photosynthetic microorganism is at least one of a bacterium and algae;

the photosynthetic microorganism is a cyanobacterium;

the cyanobacterium is *Synechococcus*;

the cyanobacterium is *Synechococcus elongatus*;

the photosynthetic microorganism is a genetically-engineered, direct biofuel-producing microorganism;

the photobioreactor includes a microfluidic chip in or on which a plurality of the optical waveguides are disposed;

the microfluidic chip is in the form of a high aspect ratio (thin) sheet;

the high aspect ratio (thin) sheet is corrugated;

the optical waveguide is a sheet waveguide;

the sheet waveguide is corrugated;

the selected photosynthetic microorganism is in the form of an adsorbed single layer of the microorganism;

the photobioreactor includes an artificial adhesive disposed intermediate the outer surface of the waveguide and the selected photosynthetic microorganism such that the microorganism is purposefully adhered to the outer surface of the waveguide.

An embodiment of the invention is directed to a method for optically exciting a photosynthetic microorganism for generating a biofuel, a biofuel pre-cursor, or a biomass from the optically-excited photosynthetic microorganism. The method include the steps of providing an optical waveguide having an outer surface; inputting optical radiation to the optical waveguide; propagating the optical radiation in the optical waveguide; generating an evanescent optical field adjacent the outer surface of the optical waveguide from the optical radiation propagating in the optical waveguide; providing a photosynthetic microorganism within the evanescent optical field of the optical waveguide; and driving photosynthesis in the microorganism by irradiating at least a portion of a thylakoid membrane of the photosynthetic microorganism with the evanescent optical field. According to various non-limiting, exemplary aspects:

the step of providing an optical waveguide further comprises providing a prism waveguide;

the step of inputting optical radiation to the optical waveguide further comprises directly injecting light from a laser into a prism waveguide in a manner to propagate the light by total internal reflection;

injecting light in a wavelength range 600 nm<λ<700 nm;

the step of providing a photosynthetic microorganism within the evanescent optical field of the optical waveguide further comprises providing the photosynthetic microorganism adjacent the outer surface of the optical waveguide in a region extending not more than about five microns (5 μm) from the outer surface of the optical waveguide;

the step of providing a photosynthetic microorganism within the evanescent optical field of the optical waveguide further comprises providing an adsorbed layer of the microorganism on the outer surface of the optical waveguide;

providing a plurality of the optical waveguides disposed in a side-by-side array configuration;

providing a photobioreactor enclosure having an input and an output, inside of which a plurality of optical waveguides are disposed, wherein the photobioreactor enclosure is characterized by a plurality of optically-dark fluid channels created by a void space surrounding the plurality of optical waveguides;

providing a microorganism nutrient media in the plurality of optically-dark fluid channels; and harvesting a biofuel, a biofuel pre-cursor, or a biomass from the photobioreactor;

the step of providing a photosynthetic microorganism further comprises providing a free-floating microorganism media within a photobioreactor enclosure;

inputting solar optical radiation to the optical waveguide;

providing a controller and controlling a parameter of the optical radiation input to the optical waveguide;

providing a suitable photosynthetic microorganism and directly harvesting a biofuel from the photobioreactor;

providing a suitable photosynthetic microorganism and harvesting a biofuel precursor from the photobioreactor;

providing a suitable photosynthetic microorganism and harvesting a biomass from the photobioreactor.

An aspect of the invention is directed to an optofluidic photoreactor. In a particular embodiment the photoreactor includes a photoreactor enclosure having a fluid inlet and a fluid outlet; a plurality of optical waveguides disposed in a spaced relationship in the photoreactor enclosure, each optical waveguide having an optical input and characterized by an evanescent optical field confined along an outer surface of each optical waveguide produced by input radiation propagating in said each optical waveguide; a plurality of fluidic reaction channels formed of the regions intermediate the plurality of optical waveguides disposed in spaced relationship in the enclosure adapted to transport a photoactive reagent; and a photoactive material disposed substantially only within the evanescent field of each optical waveguide. In various non-limiting embodiments, the photoreactor may further include some or all of the following limitations, features, characteristics alone or in various combinations.

wherein the optical waveguides are unclad optical fibers;

wherein the optical waveguides have an irregular shape;

wherein the optical waveguides are multi-mode optical fibers or rods;

wherein the plurality of fluidic reaction channels are optically-dark in the absence of said evanescent fields;

wherein the optical waveguides comprise prism waveguides;

wherein the optical input is one of a laser and an LED light input;

wherein the optical input is a solar radiation input;

further comprising a controller operably connected to the photoreactor enclosure;

wherein the optical waveguides are sheet/slab waveguides;

wherein the optical waveguides further comprise light scattering characteristics including at least one of a deposited material, a printed or lithographic pattern, and a mechanically or chemically etched surface;

wherein the photoactive reagent comprises carbon dioxide and water, in liquid and/or gaseous phases;

wherein the photoactive material is any material that can perform the conversion of carbon dioxide and water into at least one carbon monoxide, hydrogen, methane, methanol, formic acid, formaldehyde, ethanol, and larger hydrocarbons including at least one of butane, heptane and octane using optical energy;

wherein the photoactive material is a thin film of a photocatalyst;

wherein the photoactive material is a nanoparticle catalyst.

An embodiment of the invention is a method to optically activate a photoactive material in a photoreactor to convert carbon dioxide and water into another molecule that may be useful as a fuel or a chemical feedstock. In an exemplary embodiment the method includes the steps of providing a photoreactor that includes a photoreactor enclosure having a fluid inlet and a fluid outlet; a plurality of optical waveguides disposed in a spaced relationship in the photoreactor enclosure, each optical waveguide having an optical input and characterized by an evanescent optical field confined along an outer surface of each optical waveguide produced by input radiation propagating in said each optical waveguide; a plurality of fluidic reaction channels formed of the regions intermediate the plurality of optical waveguides disposed in spaced relationship in the enclosure adapted to transport a photoactive reagent; and a photoactive material disposed substantially only within the evanescent field of each optical waveguide; providing the photoactive reagent including carbon dioxide and water, in liquid and/or gaseous phases, in the fluidic reaction channels; and inputting light having a wavelength at which the photoactive material is sensitive to induce a conversion of the photoactive reagent into at least one of carbon monoxide, hydrogen, methane, methanol, formic acid, formaldehyde, ethanol, and larger hydrocarbons including at least one of butane, heptane and octane.

Additional features and advantages of the invention will be set forth in the detailed description that follows, and in part will be readily apparent to those skilled in the art from that description or recognized by practicing the invention as described herein according to the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 6A a schematic cross sectional illustration showing evanescent coupling of a photosynthetic bacterium on the surface of a waveguide. The characteristic decay of the light intensity, as plotted at the right of the figure, is on the order of the cell minor diameter size; FIG. 6B a schematic illustration of an experimental setup to generate the evanescent wave at the surface of a prism optical waveguide. The input beam is Gaussian and the evanescent field resulting from total internal reflection is elliptical in shape, as shown;

FIG. 9A: plot of the penetration depth as a function of incident laser angle for a glass-media interface. Penetration depth is defined as the location where field intensity drops $e^{-2}$, or 87%, from that at the surface.

The dashed line indicates a penetration depth of 1 μm occurring at $\theta_{i2}=\theta_C+0.074°$, and the geometry of *S. elongatus* is shown inset for reference; FIG. 9B: surface plot of evanescent field, 1 μm from the surface, with power intensity plotted to indicate the photoinhibited, growth, and negligible-growth regions, based on thresholds measured for radiant light. Based on these values an elliptical ring pattern of growth is predicted, as shown by the useful portion of the power spectrum shown in (green) shaded region 2. The vertical line plot indicates the useful light intensity decay with distance, according to illustrative aspects of the invention;

FIGS. 10A-10C: Images of cyanobacteria growth patterns resulting from evanescent excitation at the glass-media interface for incident light powers of 1 mW, 0.5 mW, and 0.25 mW, respectively. The elliptical growth patterns correspond to the evanescent field geometry, and show distinct regions of photoinhibition (centre), and growth, surrounded by negligible growth; FIGS. 10D-10F: Corresponding growth profiles for each light power with the corresponding evanescent field intensities plotted at the surface, 1 μm above the surface, and as a 5 μm average. The power range determined from the direct radiation experiments (FIG. 7B) is shown by the red band for reference. The full-width at half maximum indicating growth onset is observed at 1 μm intensity levels of 79±10 $W/m^2$, and observed at 60±8 $W/m^2$ for the 5 μm average light intensity. These values bracket the 66 $W/m^2$ threshold determined for radiant light at this wavelength, according to illustrative aspects of the invention.

FIG. 11A is a schematic cross sectional view of a sheet/slab waveguide photoreactor enclosure; FIG. 11B is a schematic cross sectional view through section A-A of FIG. 11A showing a plurality of stacked sheet/slab waveguides and in detail B, thin film photoactive material deposited on the outer surfaces of the waveguides, the fluidic channels between the stacked waveguides, and the location of the evanescent field emanating from the surfaces of each waveguide; FIG. 11C is a schematic perspective view of a stacked sheet/slab waveguide optofluidic photoreactor, according to exemplary aspects of the invention.

DETAILED DESCRIPTION

Reference will now be made in detail to the present exemplary embodiments of the invention, examples of which are illustrated in the accompanying drawings. Wherever possible, the same reference numbers will be used throughout the drawings to refer to the same or like parts.

Figure 1:
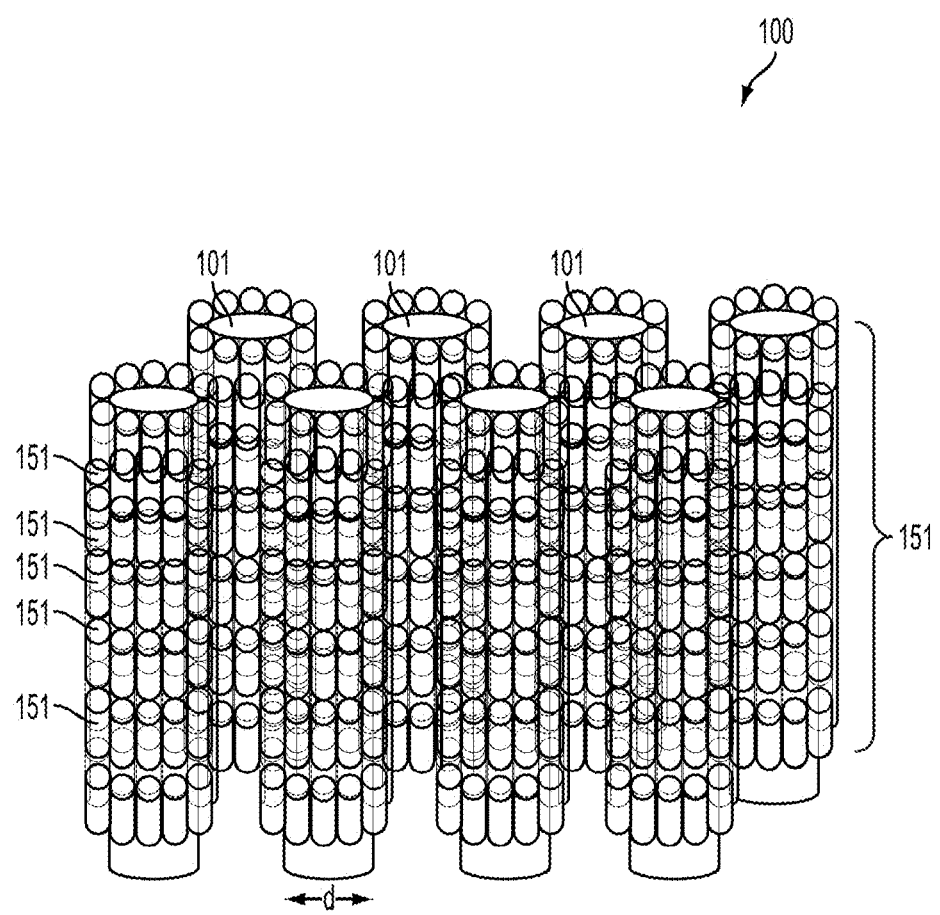
FIG. 1 schematically illustrates in perspective view an array of optical waveguides in the form of unclad optical fibers and a layer of algae disposed on the outer surface of each of the fibers, according to an illustrative embodiment of the invention.
Figure 3:
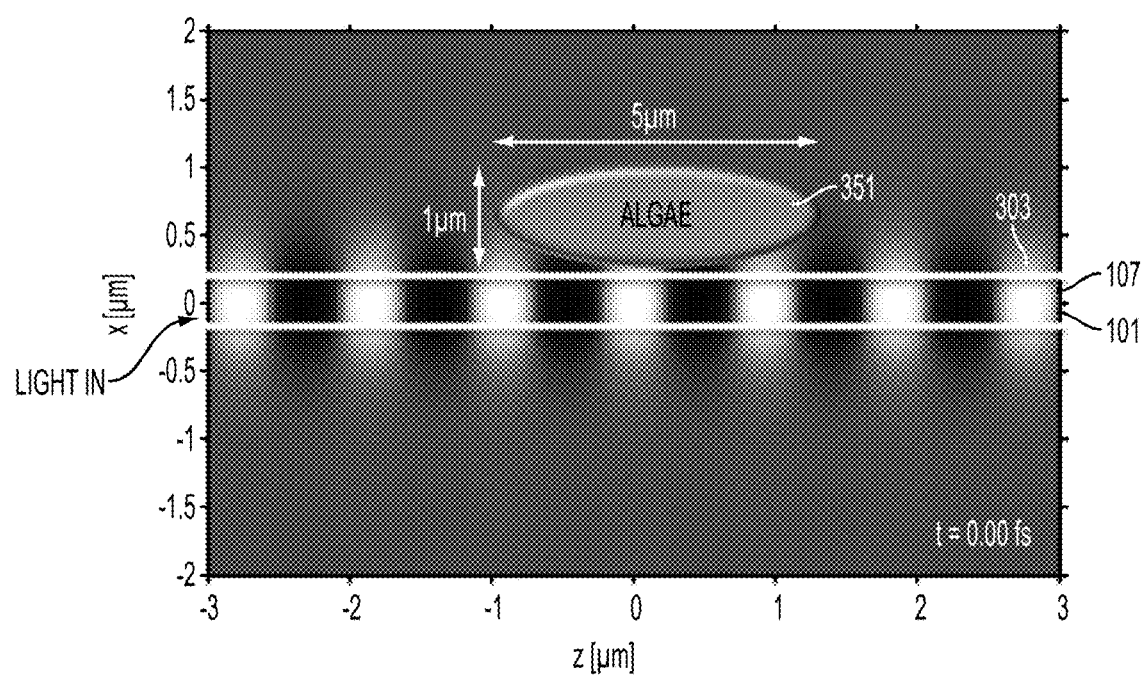
FIG. 3 is a schematic view in cross section showing the evanescent field generated from an optical waveguide as illustrated in FIG. 1 and a *Synechococcus elongatus* cyanobacterium (algae) disposed on the surface of the waveguide being irradiated by the evanescent field, according to an illustrative embodiment of the invention.

FIG. 1 schematically illustrates in perspective view an array of optical waveguides 100 in the form of unclad optical fibers 101 having a diameter, d, where 10 μm≤d≤100 μm, and a single layer of algae 151 disposed on the outer surface of each of the fibers. By propagating light in the optical fibers, an exponentially decaying optical field (referred to as an evanescent field) 303 is created over the surface of the optical fiber. FIG. 3 is a schematic view in cross section showing the evanescent field 303, and a *Synechococcus elongatus* cyanobacterium (algae) 351 adsorbed on the surface 107 of the waveguide 101 being irradiated by the evanescent field. In a non-limiting alternative aspect, the bacteria may be artificially attached to the waveguide surface with a suitable adhesive material.

Figure 2:
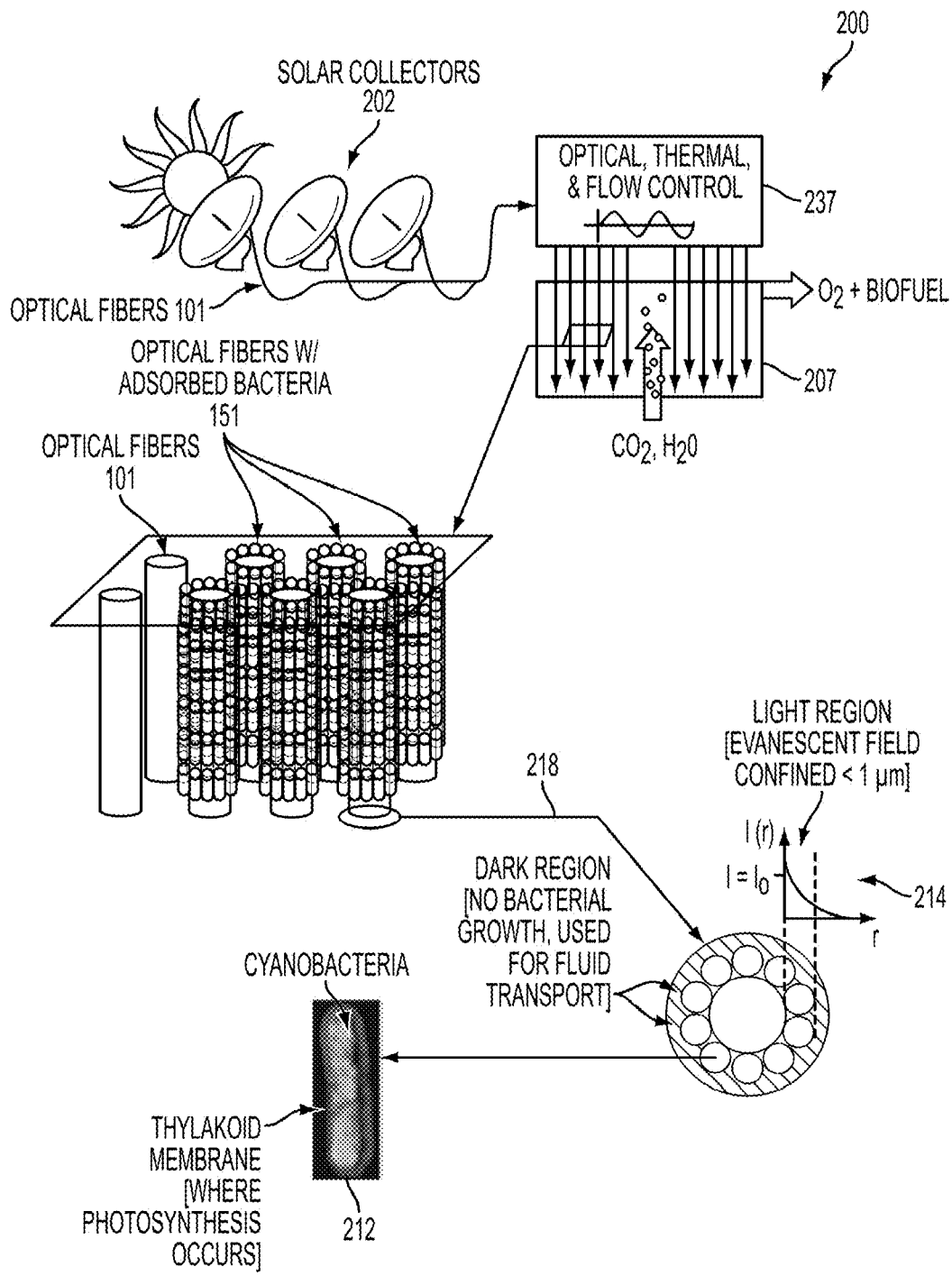
FIG. 2 is a schematic overview of a photobioreactor system utilizing the array of optical waveguides shown in FIG. 1, according to an illustrative embodiment of the invention.

FIG. 2 illustrates a photobioreactor system 200 in which solar radiation is collected (202) and coupled into the optical fibers than run through the reactor volume in a reactor enclosure 207. The photosynthetic mechanics of the cyanobacteria is contained in the thylakoid membranes (~100 nm) that surround the cyanobacteria, as illustrated in the inset 212. The evanescent field extends up to about 1 μm from the unclad fiber surface (FIG. 3) and provides the proper light intensity, $I_O$ (see 214, FIG. 2), to the bacteria. Due to the exponential decay of the evanescent field, as illustrated by the graph inset 214, a dark region 218 occurs in the interstitial space between the fibers, which serve as fluid channels (see also FIG. 4). These fluid channels can be used for transport of $CO_2$ and media to the bacteria, and for the collection of produced biofuel. The use of the evanescent field allows for the optimum utilization of light by the bacteria and for enhanced volume utilization for the reactor as a whole.

Figure 4:
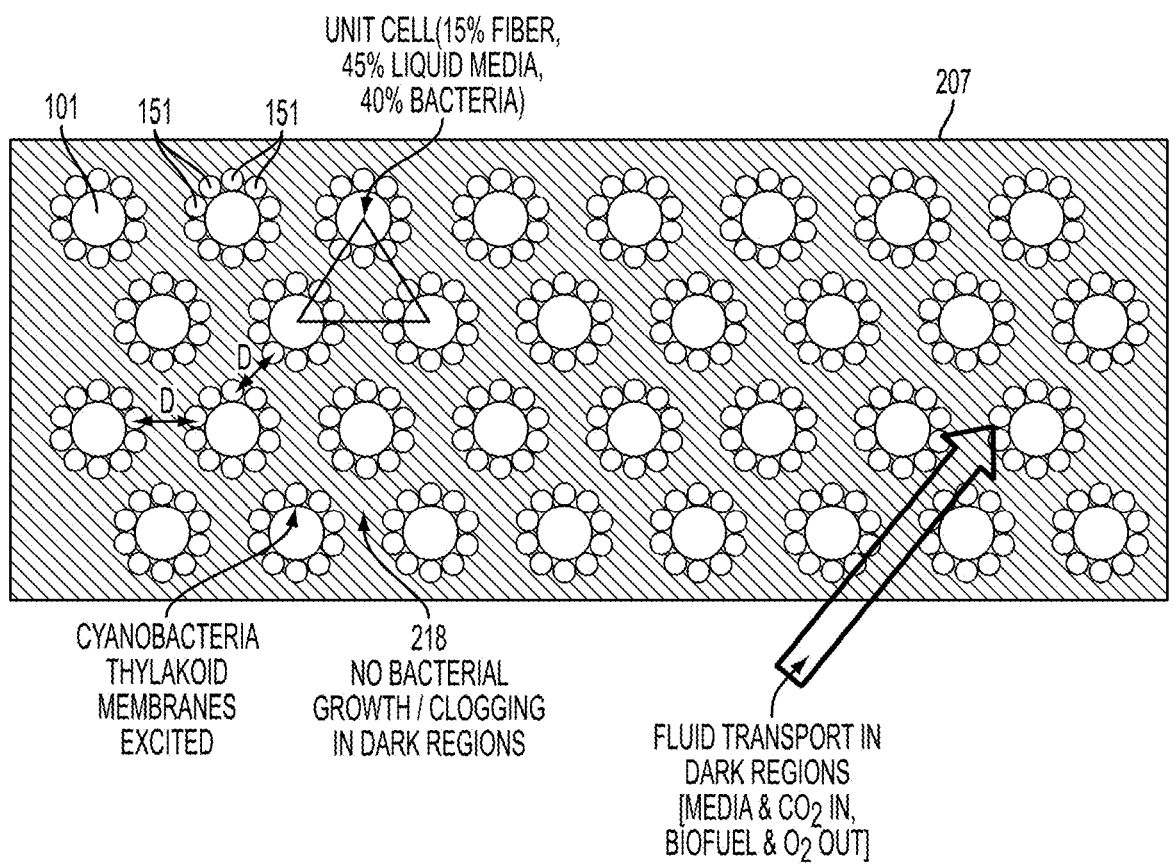
FIG. 4 shows a schematic top view of the photobioreactor enclosure containing the array of optical fibers with adsorbed photosynthetic bacteria and the dark or void regions (fluid channels) where the evanescent field does not penetrate, according to an illustrative embodiment of the invention.

FIG. 4 shows a schematic top view of the photobioreactor enclosure 207 containing the array of optical fibers 101 with adsorbed photosynthetic bacteria 151 and the dark or void regions (fluid channels) 218 where the evanescent field 303 does not penetrate. The fibers have a center-to-center intra-waveguide separation, D, where d≤D≤1.5 d.

FIG. 2 further illustrates a control component 237 that enables parameters including, but not limited to, wavelength, intensity, and duty cycle of light in the fibers to be tuned with precision such that the bacteria are optimally exposed.

For the direct conversion of $CO_2$ to biofuel, genetically modified *S. elongatus* SA665, produced at UCLA, has shown the ability to directly convert $CO_2$ to isobutyraldehyde, which may be converted to isobutanol (a gasoline substitute), at area-wise efficiencies comparable or greater to current biofuel production strategies.

Figure 5:
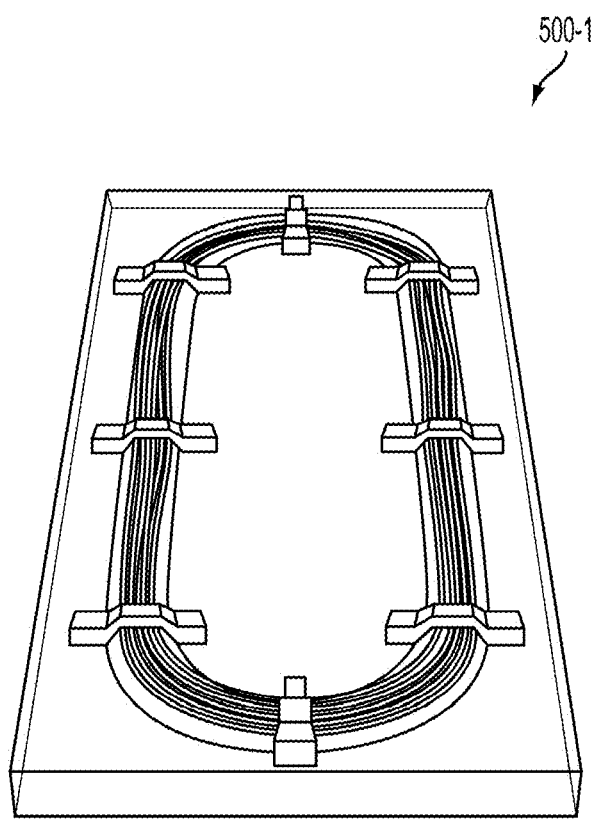
FIG. 5 is a photo of a bench-top optical fiber-based photobioreactor according to an exemplary embodiment of the invention.

An estimate of achievable density for the illustrated optofluidic bioreactor architecture is useful for comparison with current systems. A hexagonal packing of the optical fibers as shown in FIG. 4 would provide an absorbed layer of fuel producing *Synechococcus Elongatus* occupying 10% of the total volume, while the remaining 90% of the volume is required for optics and fluid. A density of 10% active bacteria by reactor volume is 4500-fold greater than demonstrated tube photobioreactors known in the art and eight orders of magnitude greater than that of a comparable pond reactor. This scaling suggests that the output of a one-story 5680 $m^2$ tube facility could be matched by a table-sized (2.5 $m^3$) optofluidic reactor 500-1 according to the embodied invention as shown in FIG. 5. While such a reactor would require a separate photocollector and associated irradiated area, the separation of reactor with collection additionally offers the ability to tailor the light spectrum to the photosynthetically active range (400-700 nm); cycle light at an optimal frequency for photosynthetic activity (typically 100 Hz); collect incident solar light at high angles as required outside of equatorial regions; and control the reactor temperature making operation feasible in colder climates where fuel demand is high, such as North America and Europe.

Detailed Exemplary Embodiment

Figure 6A:
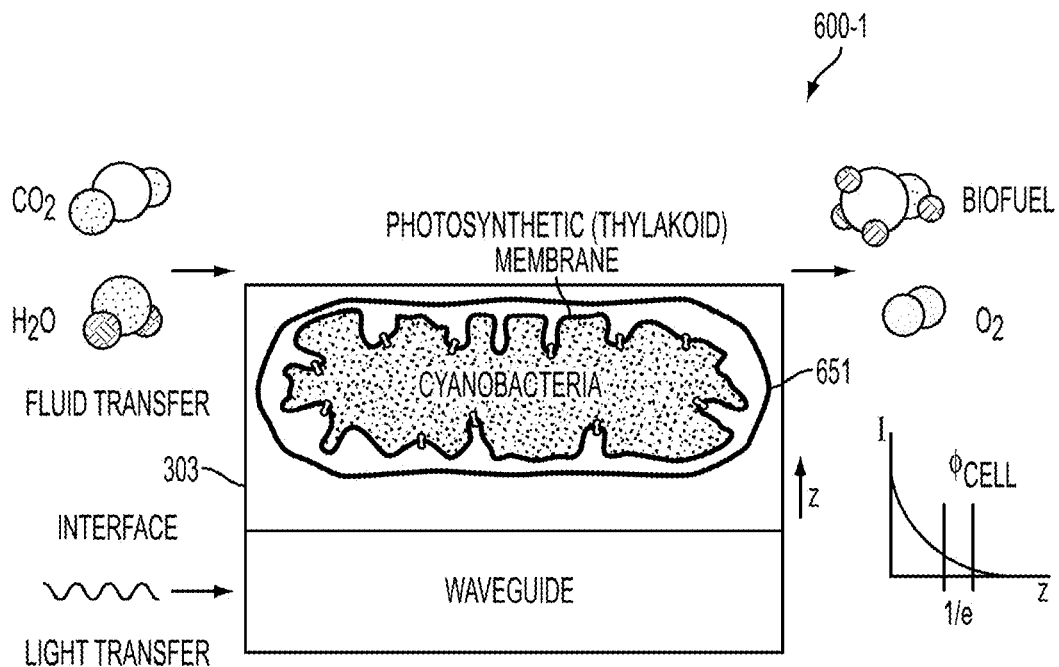
FIGS. 6A, 6B illustrates excitation process and apparatus for photosynthetic bacteria with an evanescent light field.
Figure 6B:
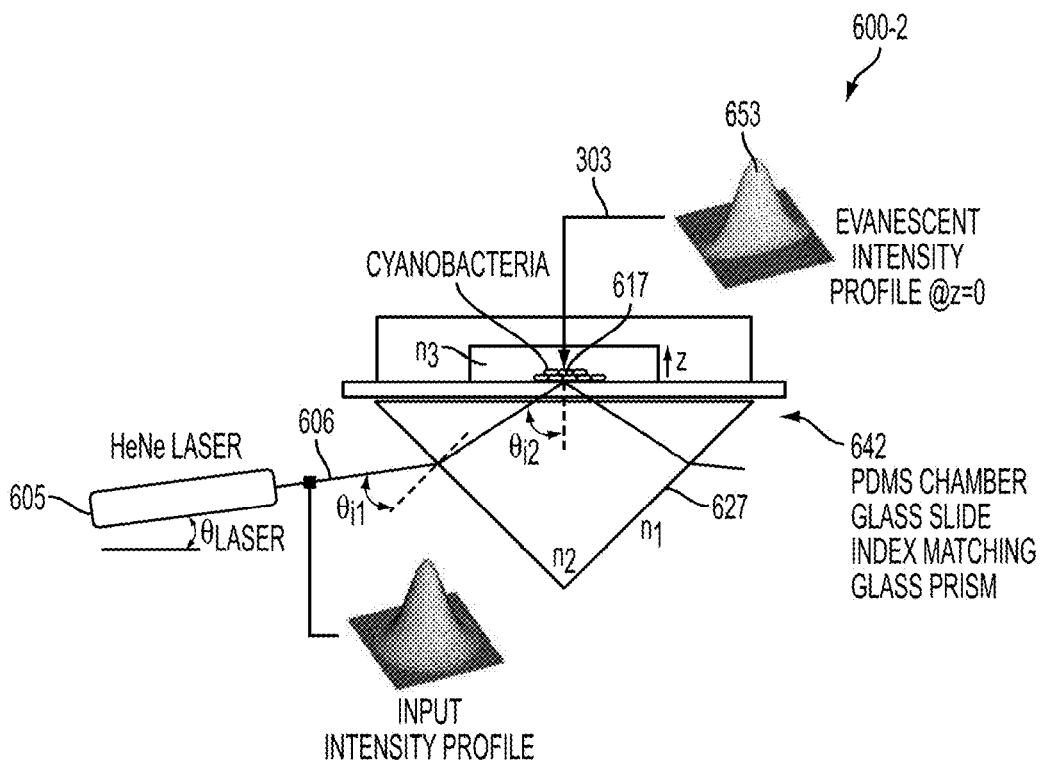

According to another exemplary embodiment and aspects thereof, FIGS. 6A and 6B, respectively, illustrate the evanescent excitation process 600-1 of a bacterium 651 and a prism waveguide-based photobioreactor 600-2 used to generate the evanescent excitation field 303. As more particularly illustrated in FIG. 6B, a prism waveguide 627 is shown in cross section. Monochromatic red (λ=633 nm) light 606 provided by a HeNe laser 605 is directly injected into the side of the prism waveguide. The evanescent field 303 is generated at the interface surface 617 of a glass slide 642 where the light is totally internally reflected. Total internal reflection, and the corresponding evanescent field, result when the light is incident at the glass-media interface at angles greater than the critical angle; i.e., $\theta_{i2} > \theta_c$. Reflecting a circular cross-section input beam creates an elliptical evanescent field profile on the prism surface at the point of reflection, as shown in the inset 653 in FIG. 6B. It will be appreciated by those skilled in the art that there are alternative ways to generate an evanescent field; however, the illustrated approach is simple and provides an evanescent light field distribution that can be reliably described with theory in all three dimensions.

In the experimental set-up of FIG. 6B, cavities to contain a bacteria culture solution were fabricated by moulding PDMS (Sylgard® 184 Elastomer Kit, Dow Corning) around a poly(methylmethacrylate) (PMMA) master to create cylindrical cavities 10 mm in diameter and 4.75 mm deep (0.373 mL). These culture cavities were bonded to the surface of a 1 mm thick BK7 glass microscope slide using oxygen plasma treatment.

Cells of the wild type *S. elongatus* (ATCC 33912) cyanobacteria were used to demonstrate the embodied invention. Cells were cultured under optimal conditions of 32-36° C. and under continuous irradiation of 50-75 $\mu E \cdot m^{-2} \cdot s^{-1}$ using fluorescent lamps. The stock culture was kept at a constant cell density (in the exponential growth phase) by regularly diluting the culture with fresh BG11 cyanobacteria growth medium (Sigma Aldrich C3061) to maintain a constant optical density of 0.2 at 750 nm ($OD_{750}$). The $OD_{750}$ was determined using a broad spectrum halogen light source (Thorlabs OSL1) and spectrometer (Edmond brc112e) and normalized to the $OD_{750}$ of fresh BG11 growth media. Samples of this culture were used in our experiments.

Once mounted to the glass plates and inoculated (dead end filling via syringe injection), the cultures were placed on the top faces of right angle BK7 prisms (Thorlabs PS908L-A), as shown in FIG. 6. Optical contact was achieved using an index matched immersion oil (Leica 11513 859). Light was coupled to the chamber from a helium neon laser (632.8 nm Thorlabs HRR020) directed toward the prism by reflecting it off a broadband dielectric mirror (Thorlabs CM1-4E; not shown) mounted to a precision rotation mount (Thorlabs CRM1P; not shown). The incident angle at the glass media interface was adjusted by changing the angle of the mirror in the rotation mount. The prism/culture assembly was mounted to a sliding stage (not shown), which allowed the laser beam to be maintained in the center of the culture chamber as the angle of incidence was varied. The prism assembly was aligned such that the reflection of the beam leaving the prism did not pass through the culture. This ensured that optical excitation of the bacteria was solely due to the evanescent field where the beam was totally internally reflected at the glass-bacteria culture interface.

Laser beam power into and out of the prism was measured using a photodiode power sensor (Thorlabs S120C) and measured once at the beginning of the experiment and once at the end. The entire experimental apparatus was optically isolated in enclosures made from 5 mm thick hardboard (Thorlabs TB4). These chambers were kept at a constant temperature of 32-36° C. for optimal cell growth rates for the duration of the evanescent growth experiments using a 950 W enclosure fan heater (CR030599, OMEGA Engineering Inc., USA).

Experimental Results and Discussion

Figure 7A:
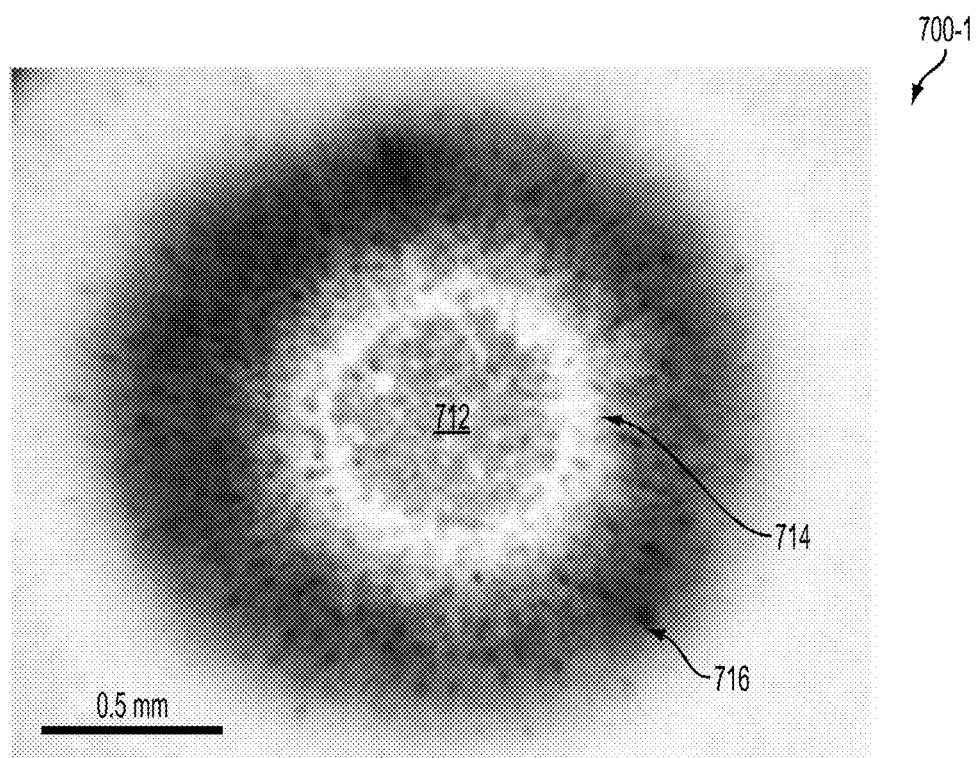
FIG. 7A: image of cyanobacteria growth pattern resulting from direct irradiation, showing distinct regions of photoinhibition (centre), growth, surrounded by negligible growth.
Figure 7B:
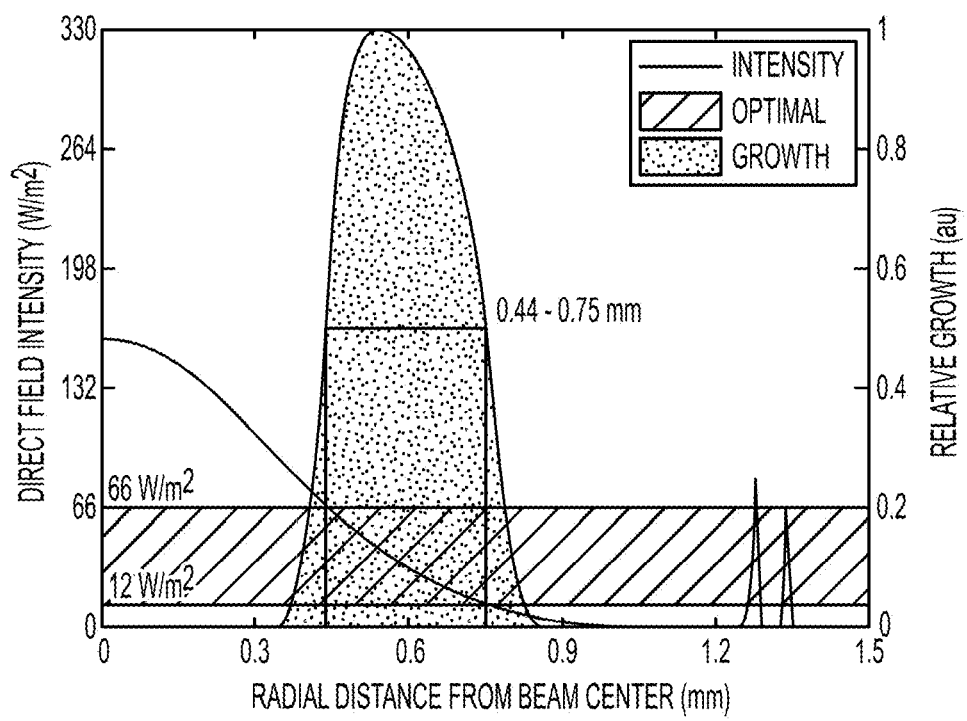
FIG. 7B: plot correlating radial growth intensity to laser light intensity. Outlying peaks beyond 1.2 mm are artifacts of the imaging setup and do not correspond to growth. FWHM thresholds on the growth region correspond to radiant light intensities of 66 $W/m^2$ and 12 $W/m^2$, shown as upper and lower bounds, respectively, according to illustrative aspects of the invention.

Cell cultures were first placed under direct laser light exposure, to establish the effectiveness of using monochromatic red ($\lambda$=633 nm) at growing *S. elongatus*, and measure cell response to direct radiation light. The beam from a Helium-Neon (HeNe) laser was passed through a culture cavity perpendicular the bottom glass slide (FIG. 6B) and the culture was left to grow for 72 hours (under conditions described above). This type of direct irradiation experiment was done for various laser powers, yielding consistent results to those shown in FIG. 7. FIG. 7A shows a typical growth ring pattern 700-1, where the effect on growth from the three distinct intensity regions 712 (center), 714 (mid), 716 (outer) is evident as shown. There is a bleached (yellowish orange in color view) region 712 in the center, a growth region 714 (green in color view) and a negligible growth outer region 716. To quantify growth in a radial profile, the image was filtered for green intensity and integrated in circumference. The resulting radial growth profile is plotted with the laser intensity profile in FIG. 7B. The threshold electric field intensities (low and high) between regions were determined from the intersection of the full width at half the maximum (FWHM) growth locations and the incident light power profile. The resulting threshold values of 66 W/m² and 12 W/m² (shown in FIG. 7B by the rectangle within the growth peak) indicate the productive growth intensities of *S. elongatus* under direct irradiation at $\lambda$=633 nm.

Figure 8:
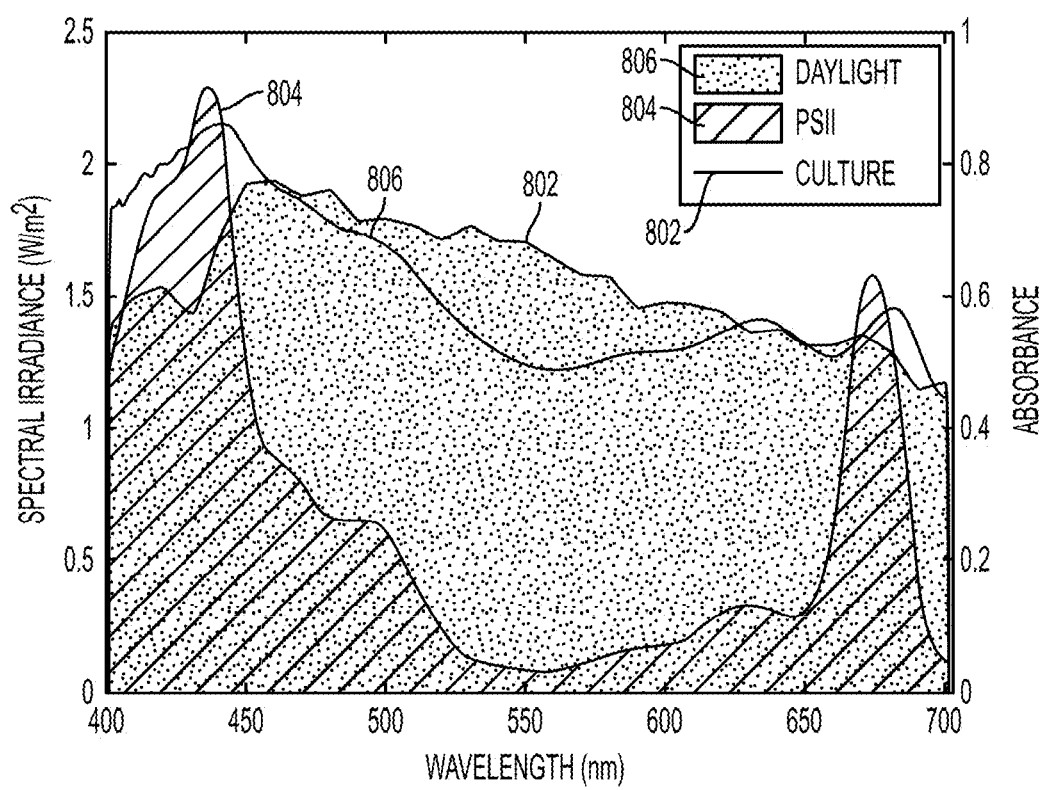
FIG. 8 graphically shows a spectral power distribution of daylight and an absorption spectrum of PSII plotted with measured absorbance of the *S. elongatus* culture. The photoinhibition threshold at $\lambda=633$ nn measured from experiments in FIG. 7 (66 $W/m^2$) correlates to established photoinhibition intensities of white light exposure, when related through the absorption spectrum shown, according to an illustrative aspect of the invention.

Relating these direct irradiation experiment results to known growth characteristics of *S. elongatus* requires determining the daylight equivalent power of red light at $\lambda$=633 nm. To do so, we compared radiometric measurements of daylight to optimal intensity ranges published in literature. At high light intensities, the rate of radiation induced damage to the cell's photosystems exceeds the cell's ability to repair itself and the result is a sharp decrease in photosynthetic activity, or photoinhibition. High light conditions that approach saturating intensities are reported as a Photosynthetic Photon Flux Density (PPFD) on the order of 150 $\mu E \cdot m^{-2} \cdot s^{-1}$ to 500 $\mu E \cdot m^{-2} \cdot s^{-1}$ in the Photosynthetically Active Radiation (PAR) wavelength range (400-700 nm), or 10%-25% of full daylight. To convert the photosynthetic photon flux density to radiometric units (i.e. W/m²), the optical power of full daylight was measured at 635 nm to be 1.37 W/m² (48°25'43" N, 123°21'56" W). The spectral power distribution of normal daylight 806 was then calculated from this set point and the relative spectral power distribution defined by CIE Standard Illuminant D65, as shown in FIG. 8. Total full daylight irradiance of photosynthetically active radiation was calculated to be 472 W/m², which corresponds to a photosynthetic photon flux density of 2137 $\mu E \cdot m^{-2} \cdot s^{-1}$. This value was independently confirmed by a QSR-2100 (Biospherical Instruments Inc.) light meter measurement of 2100-2300 $\mu E \cdot m^{-2} \cdot s^{-1}$. Also shown in FIG. 8, is the absorption spectrum 804 for Photosystem II (Sugiura M & Inoue Y (1999) Highly Purified Thermo-Stable Oxygen-Evolving Photosystem II Core Complex from the Thermophilic *Cyanobacterium Synechococcus elongatus* Having His-Tagged CP43, *Plant Cell Physiol.* 40(12):1219-1231). Photosystem II (PSII) is the link in the photosynthetic pathway most susceptible to light induced damage and is the first point of failure in high light environments. The characteristic shape of the published absorption spectrum can also be observed in the measured absorption spectrum of the sample culture 802 ($OD_{750}$ of 0.37), most notably at the ~450 nm, 630 nm and 670 nm peaks as plotted FIG. 8. Absorption in the red region of the spectrum contributes most significantly to photosynthesis while absorption of lower wavelengths is due to the presence of molecules not directly involved in the electron transport process. Under normal daylight conditions, *S. elongatus* PSII absorbs 30 W/m² of red light (600 nm<λ<700 nm) determined by weighing the spectral power distribution for daylight by the absorption spectrum of PSII and integrating across the red portion of the spectrum. In order to deliver an equivalent amount of energy using monochromatic laser light at λ=633 nm, the ability of PSII to absorb at that wavelength needs to be considered to determine the appropriate corresponding laser power. In this case, PSII absorbs approximately 13% of 633 nm light, which requires a laser power of 230 W/m² to simulate full daylight conditions. The threshold measured in the direct irradiation experiments, 66 W/m², therefore suggests that ~28% of full daylight is the upper limit for our cultures before severe photoinhibition occurs. This value agrees well with the upper bounds of what are considered high-light conditions as reported in the literature.

Figure 9A:
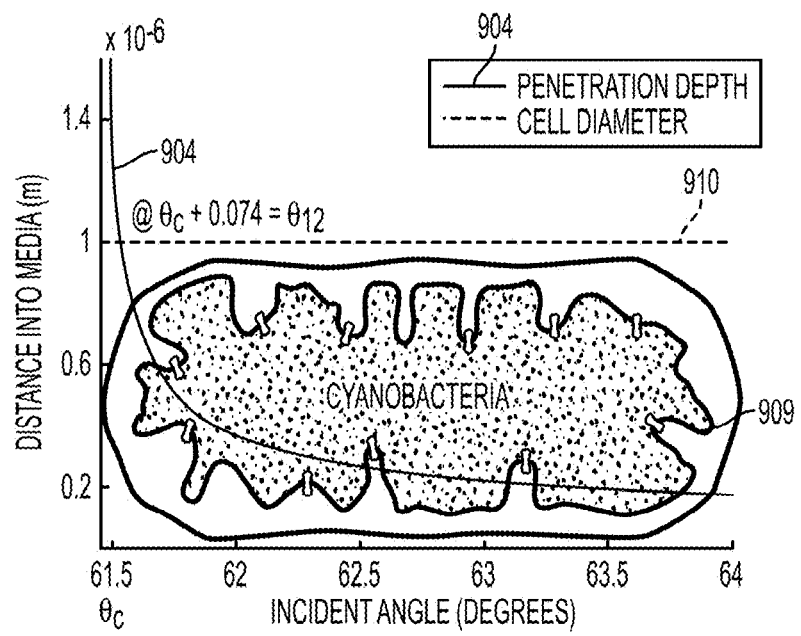
FIGS. 9A, 9B illustrates the theoretical light intensity distribution in the evanescent light field, and corresponding predicted growth patterns.

The light intensity distribution in an evanescent light field varies both in the plane of the surface and depth-wise into the media. Established theory was applied to describe the evanescent electric field intensity and used to correlate field strength to experimental growth results. FIG. 9A shows the penetration depth 904 (y-axis) of the evanescent light field as a function of incident angle (x-axis). Here, the penetration depth is quantified as the location where the field intensity drops $e^{-2}$, or 87%, of the peak intensity at the surface. The geometry of *S. elongatus* is shown inset (909) in FIG. 9A for reference, and the dashed line 910 indicates a penetration depth of about 1 μm, which occurs at an angle of incidence of $\theta_{i2}=\theta_c+0.074°$. As shown, the penetration depth of the evanescent field is a strong function of incident angle, with values corresponding to the inherent lengthscale of the bacterium occurring only near the critical angle (below 0.5° past critical).

Figure 9B:
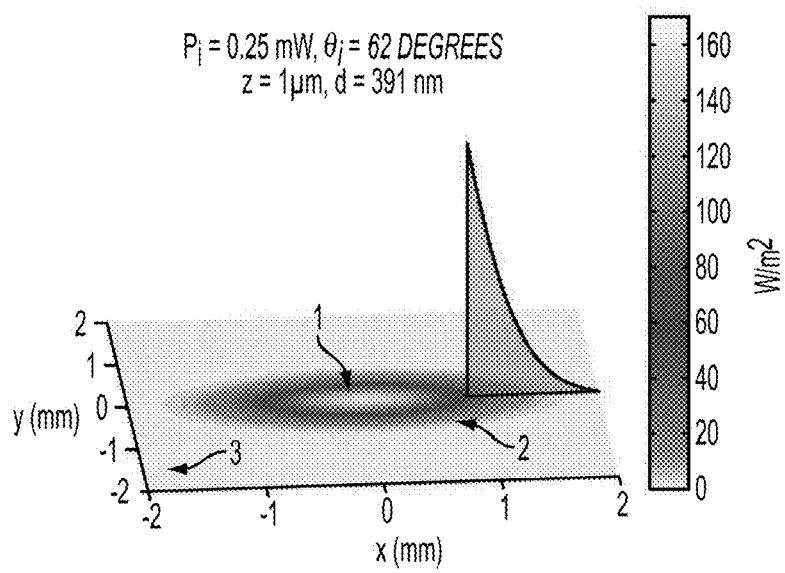

FIG. 9B shows the predicted evanescent field intensity in the plane, and the characteristic oval shape for an incident 0.5 mm diameter Gaussian beam at λ=633 nm. The intensity values indicated correspond to the evanescent light intensity at 1 μm from the glass-media interface, with an incident angle of 62° ($\theta_{i2}=\theta_c+0.5°$) and penetration depth of 400 nm. Based on the above-determined threshold light intensity for the red light employed here (66 W/m², at 633 nm), the expected growth regions can be predicted based on the calculated evanescent field intensity. As shown in FIG. 9B, in region 1 the evanescent field intensity exceeds the red component of 10% daylight and would be expected to lead to photoinhibition in a radiant light system. This analysis would predict an elliptical ring pattern of growth, as shown by the useful portion of the power spectrum, region 2 (green shading in color diagram). The vertical line plot indicates the useful light intensity decay with distance. Relatively intense growth is expected near the inside boundary where useful light intensities are high, and growth rates would decay with the light intensity outward. Although the sharpness of the inside edge of the growth profile is an artifact of the threshold boundary condition, the model provides the predicted pattern of growth for a photosynthetic microorganism cultured in this evanescent field.

Figure 10A:
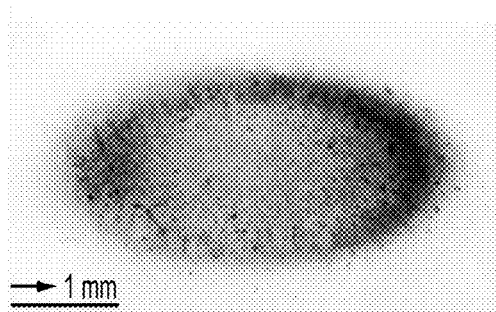
FIGS. 10A-10F illustrates the growth of photosynthetic bacteria using evanescent light.
Figure 10D:
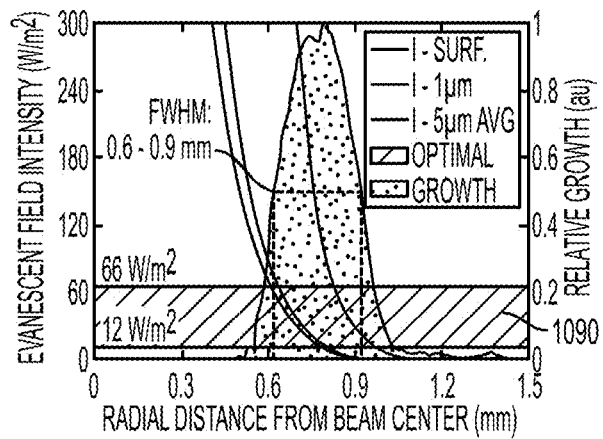
Figure 10B:
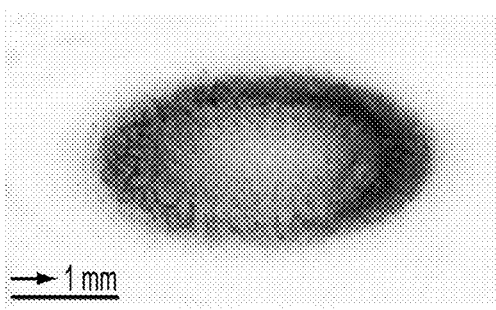
Figure 10E:
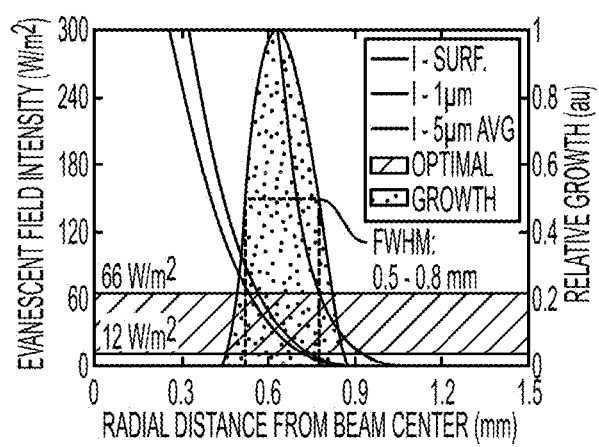
Figure 10C:
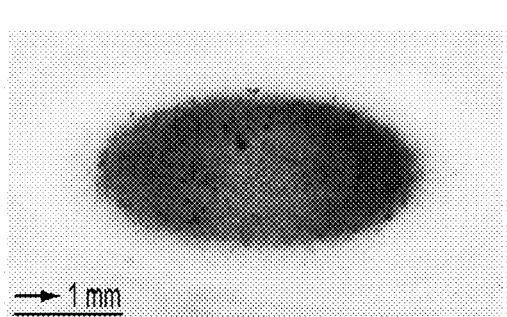
Figure 10F:
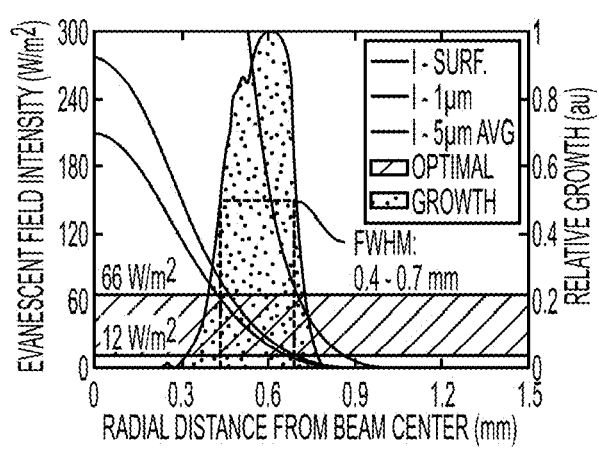

Evanescent light based excitation of the culture was performed using the experimental setup shown in FIG. 6B. Three laser powers were employed (1 mW, 0.5 mW, 0.25 mW) with incident laser angles of 62° ($\theta_{i2}=\theta_c+0.5°$), and total internal reflection was ensured by measuring the output intensity. Each experiment was performed in triplicate and the cultures were exposed to the evanescent field for 72 hours. FIGS. 10A-C show substantial bacteria growth in response to the evanescent light field at the surface of the glass-media interface. The growth patterns showed the elliptical shape mirroring the evanescent light field intensity, and delineate the three characteristic regions (photoinhibition, growth, negligible-growth), providing data on the onset of growth under evanescent light. As the laser power was reduced (FIGS. 10A to C), the radial distribution moved inward, consistent with the change in the light intensity profile. To relate the observed growth to the evanescent field intensity, the images were filtered for green intensity, scaled along the axis of the beam, and integrated to provide growth profiles. FIGS. 10D-F show the growth profiles for each light power with the corresponding evanescent field intensities plotted at the surface, 1 μm above the surface, and as a 5 μm average. Due to rapidly decaying nature of the evanescent field, the surface intensity is much higher than that at 1 μm above the surface, which is also similar to the average intensity over the first 5 μm (both 1 μm and 5 μm are relevant lengthscales of this rod-shaped bacteria). The power range determined from the direct radiation experiments is shown by the red band 1090 for reference. The onset of growth occurs at a radial location where the evanescent light intensity—as measured at 1 μm and as a 5 μm average—drops to a value corresponding to the threshold of 66 W/m², established from direct radiation experiments. As the total intensity of light is decreased (FIGS. 10A-C and D-F), the location of the onset intensity moves inward, and remains consistent with the predicted power curves. Specifically, the full-width at half maximum, indicating growth onset, is observed at 1 μm intensity levels of 79±10 W/m², and observed at 60±8 W/m² for the 5 μm average light intensity. These results both demonstrate growth of photosynthetic bacteria using evanescent light, and provide metrics for their successful cultivation within this unique light field.

The growth patterns shown in FIG. 10 show some downbeam bias, that is, growth intensity increases with distance from the laser source. When the cells interact with the evanescent field near the surface, some of the light is absorbed and utilized, while some of the light is scattered. The light will be scattered preferentially in the direction of the beam. With the present experimental setup, this scattered light would contribute to higher growth rates, and thicker biofilms, on the downbeam side of the ring pattern. This effect was noticed in most cases with downbeam growth biases of 1%, 8%, and 15% for the 0.25 mW, 0.50 mW, 1.0 mW cases plotted in FIG. 10. Although the extent of this bias varied between trials, and some trials showed negligible, and even a small upbeam bias, the effect was in general small and in all cases less than 15%. While it is likely that downbeam bias and secondary scattering effects influence growth, the relative symmetry of the growth patterns indicates that the downbeam scattering effect is minor.

The additional effect of light penetration depth was investigated using incident light at larger angles past critical ($\theta_c<\theta_{i2}<\theta_c+5$). At angles greater than 0.5° over critical (as plotted in FIG. 10), however, only faint growth rings were observed. We attribute the lack of growth at larger angles to the change in penetration depth, which diminishes rapidly with increasing incident angle, as shown in FIG. 9A. Specifically, the penetration depth corresponds to the minor-dimension of the rod-shaped bacterium (1 μm) only at angles less than $\theta_c+0.074°$. These results are thus consistent with the observed evanescent growth patterns in that the penetration depth approached the cell diameter only at small angles away from critical.

We have thus demonstrated an evanescent-light based approach to deliver light on the lengthscale of cyanobacteria for photosynthesis. In addition to demonstrating cultivation of bacteria in the evanescent field, analysis of the growth pattern provides guidelines for determining appropriate evanescent light exposure conditions from known radiant light response. Growth can be predicted based on these metrics both with respect to light penetration depth and light intensity. In the context of photobioreactor technology, this approach to light distribution differs from conventional approaches of bulk irradiation in that it offers a means of controlling the energy delivered to individual cells rather than bulk cultures. A photobioreactor architecture based on the embodied evanescent light delivery approach could take several forms. For example, one approach could be to leverage the low cost and relative ubiquity of fiber optic technology in a reactor with a dense network of bacteria-absorbed fibers, or fabric, in a large media vessel. Paired with recent advances in the genetic modification of cyanobacteria for direct production of fuels such as ethanol or isobutyraldehyde/isobutanol, such a strategy presents new opportunities for solar fuel generation.

FIG. 11A is a schematic cross sectional view of a sheet/slab waveguide photoreactor 1100 enclosure 1101. As further illustrated in FIG. 11C, the enclosure includes a liquid nutrient inlet 1105, a liquid photoproduct output 1106, a gas nutrient inlet 1107, and a gas photoproduct outlet 1108. FIG. 11B shows a plurality of stacked sheet/slab waveguides 1110 and, in detail B, thin film photoactive material 1112 deposited on the outer surfaces 1113 of the waveguides, the fluidic nutrient channels 1116 between the stacked waveguides, and the location of the evanescent field 1120 emanating from the surface of each waveguide. The embodied apparatus provides an optofluidic reactor to deliver light to photoactive materials to perform chemical reactions that convert a photoactive reagent 1118 (e.g., carbon dioxide and water) into other molecules that may be useful as fuels or chemical feedstocks. These molecules can include carbon monoxide and hydrogen, as well as liquid and gas hydrocarbon molecules such as methane, methanol, formic acid, formaldehyde, ethanol, and larger hydrocarbons including at least one of butane, heptane and octane using optical energy. Particularly advantageous is the ability to produce liquid hydrocarbons like methanol that are useful as fuels or chemical feedstocks.

Energy to enable the reaction enters the reactor 1100 in the form of light (1124, FIG. 11C), where it is guided to the reaction sites through dielectric slab waveguides 1110. These can be either broadband or can support specific wavelengths of light optimized for use with a particular photoactive material 1112. The waveguides can be composed of glass or ceramic materials, polymer materials, or some combination. Light guided through these waveguides produces an evanescent field 1120 at the interface of the waveguide with a reaction channel 1116. One skilled in the art will appreciate that the waveguides need not be limited to sheet/slab waveguides, which provide large surface areas for the photoactive materials in contact with them and the evanescent field; rather, various waveguides such as unclad fibers and multimode fibers or rods, and irregular shaped waveguides, for example, may also be used.

The amount of light leaking out into this evanescent field can be enhanced and controlled through the use of scatterers, which can take the form of deposited material, patterned through either a printing or lithography process, mechanically etched scatterers, such as those produced by sanding or otherwise mechanically roughening the waveguide surface, or chemically etched scatterers, produced by treating the (glass) surface with fluoride based compounds and acids.

The photoactive reagent media 1118 in the reaction channel 1116 can be either liquid, such as water with dissolved carbon dioxide, or in the gas phase containing both gaseous carbon dioxide and water vapor, as in flue gas. Gas reagent delivery may be enhanced through the use of hollow fiber membranes. The photoactive element 1112 may be any material that can perform the conversion of carbon dioxide using optical energy. This can be in the form of a thin film of a photocatalyst, or a nanoparticle catalyst either supported on the surface 1113 or fluidized within the evanescent field illuminated region 1120. Many different types of photocatalyst materials have been proposed in the literature, and this reactor configuration is not specific to any one type.

There are several key advantages gained by performing the reaction with an inorganic catalyst as opposed to a photosynthetic organism, as disclosed herein above. First, while living organisms require a relatively narrow range of temperatures, optical intensities, and solution environments to survive, inorganic catalysts are less sensitive to these environmental requirements. This allows the reaction to be operated at higher temperatures and pressures, improving the reaction rates, allowing the possibility of gas phase reactions which extend applicability to flue gas streams, and improving selectivity for higher value molecules. It also improves energy utilization with a broadband input light source, like sunlight, as photons not used directly are absorbed as heat in the reactor, providing a secondary energy input to the reaction. Second, this allows the input optical intensity to be higher and allows for working with higher energy photons in the ultraviolet range that can damage living cells. Third, the photocatalyst requires no nutritional input or maintenance when not in use. Fourth, unlike a living organism which must divert energy to performing its biological functions, all of the energy input to the catalyst can in principle be used in the reaction. Use of an inorganic catalyst also removes the need to work around natural selection pressures that can drive photosynthetic cultures to lower productivities over time. Fifth, inorganic materials are compatible with sterile operating environments, reducing the risk of contamination and the need for treating reactors with antibiotics, which could have negative environmental impacts.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. An optofluidic photoreactor, comprising:
   a photoreactor enclosure having a fluid inlet and a fluid outlet;
   a plurality of optical waveguides disposed in a spaced relationship in the photoreactor enclosure, each optical waveguide having an optical input and characterized by an evanescent optical field confined along an outer surface of each optical waveguide produced by input radiation propagating in said each optical waveguide;
   a plurality of fluidic reaction channels formed of the regions intermediate the plurality of optical waveguides disposed in spaced relationship in the enclosure adapted to transport a photoactive reagent; and
   a photoactive material disposed substantially within the evanescent field of each optical waveguide.

2. The photoreactor of claim 1, wherein the optical waveguides are unclad optical fibers.

3. The photoreactor of claim 1, wherein the optical waveguides are multi-mode optical fibers or rods.

4. The photoreactor of claim 1, wherein the plurality of fluidic reaction channels are optically-dark in the absence of said evanescent fields.

5. The photoreactor of claim 1, wherein the optical waveguides comprise prism waveguides.

6. The photoreactor of claim 1, wherein the optical input is one of a laser and an LED light input.

7. The photoreactor of claim 1, wherein the optical input is a solar radiation input.

8. The photoreactor of claim 1, further comprising a controller operably connected to the photoreactor enclosure.

9. The photoreactor of claim 1, wherein the optical waveguides are sheet/slab waveguides.

10. The photoreactor of claim 1, wherein the optical waveguides further comprise light scattering characteristics including at least one of a deposited material, a printed or lithographic pattern, and a mechanically or chemically etched surface.

11. The photoreactor of claim 1, wherein the photoactive reagent comprises carbon dioxide and water, in liquid and/or gaseous phases.

12. The photoreactor of claim 1, wherein the photoactive material is any material that can perform the conversion of carbon dioxide and water into at least one carbon monoxide, hydrogen, methane, methanol, formic acid, formaldehyde, ethanol, and larger hydrocarbons including at least one of butane, heptane and octane using optical energy.

13. The photoreactor of claim 1, wherein the photoactive material is a thin film of a photocatalyst.

14. The photoreactor of claim 1, wherein the photoactive material is a nanoparticle catalyst.

15. The photoreactor of claim 1, wherein the optical waveguides have an irregular shape.

16. The photoreactor of claim 1, wherein the optofluidic photoreactor comprises a dark region and a plurality of light regions when the waveguides receive an optical input.

17. The photoreactor of claim 1, wherein there is substantially no photoactive material disposed or grown outside the evanescent field of each optical waveguide.

18. A method to optically activate a photoactive material in a photoreactor to convert carbon dioxide and water into another molecule that may be useful as a fuel or a chemical feedstock, comprising:
   providing a photoreactor that includes a photoreactor enclosure having a fluid inlet and a fluid outlet, a plurality of optical waveguides disposed in a spaced relationship in the photoreactor enclosure, each optical waveguide having an optical input and characterized by an evanescent optical field confined along an outer surface of each optical waveguide produced by input radiation propagating in said each optical waveguide, a plurality of fluidic reaction channels formed of the regions intermediate the plurality of optical waveguides disposed in spaced relationship in the enclosure adapted to transport a photoactive reagent, and a photoactive material disposed substantially within the evanescent field of each optical waveguide;
   providing the photoactive reagent including carbon dioxide and water, in liquid and/or gaseous phases, in the fluidic reaction channels; and
   inputting light having a wavelength at which the photoactive material is sensitive to induce a conversion of the photoactive reagent into at least one of carbon monoxide, hydrogen, methane, methanol, formic acid, formaldehyde, ethanol, and larger hydrocarbons including at least one of butane, heptane and octane.

* * * * *